US006406666B1

(12) United States Patent
Cicha et al.

(10) Patent No.: US 6,406,666 B1
(45) Date of Patent: Jun. 18, 2002

(54) METHOD AND APPARATUS FOR VAPORIZING STERILANT HYDROGEN PEROXIDE

(75) Inventors: John Cicha, Shoreview; Terry Erickson, St. Paul; John Lees, Minneapolis, all of MN (US)

(73) Assignee: Tetra Laval Holdings & Finance, SA, Pully (CH)

( * ) Notice: Subject to any disclaimer, the term of this patent is extended or adjusted under 35 U.S.C. 154(b) by 0 days.

(21) Appl. No.: 09/788,789

(22) Filed: Feb. 20, 2001

(51) Int. Cl.[7] ............................. A61L 2/00; A61L 9/00
(52) U.S. Cl. ........................................ 422/28; 422/26
(58) Field of Search ........................ 422/26, 28, 292, 422/298, 299, 304, 305, 306, 307

(56) References Cited

U.S. PATENT DOCUMENTS

| | | | |
|---|---|---|---|
| 3,605,872 A | 9/1971 | Brault ............................ 165/1 |
| 4,241,043 A | 12/1980 | Hetzel ......................... 423/659 |
| 4,424,189 A | 1/1984 | Hick ............................ 422/27 |
| 4,512,935 A | * 4/1985 | Hilmersson et al. ........... 261/79 |
| 4,697,636 A | 10/1987 | Mellsjö ........................ 165/156 |
| 4,869,833 A | * 9/1989 | Binning et al. .............. 210/761 |
| 4,896,478 A | * 1/1990 | Reiter .......................... 53/426 |
| 5,007,232 A | 4/1991 | Caudill ......................... 53/426 |
| 5,228,505 A | 7/1993 | Dempsey ..................... 165/140 |
| 5,258,162 A | 11/1993 | Andersson et al. ............ 422/28 |
| 5,477,672 A | 12/1995 | Tsujikado et al. ........ 60/39.462 |
| 5,730,934 A | 3/1998 | Holbert ......................... 422/24 |
| 5,770,232 A | 6/1998 | Sizer et al. .................. 424/616 |
| 5,809,739 A | 9/1998 | Eno ............................. 53/167 |
| 5,809,740 A | 9/1998 | Sundby et al. ................. 53/167 |
| 5,843,374 A | 12/1998 | Sizer et al. .................... 422/24 |
| 6,037,598 A | 3/2000 | Cicha ....................... 250/455.11 |
| 6,056,918 A | 5/2000 | Palaniappan et al. ......... 422/24 |
| 6,058,678 A | 5/2000 | Lees ........................... 53/426 |
| 6,101,786 A | 8/2000 | Lees ........................... 53/167 |

* cited by examiner

*Primary Examiner*—Robert J. Warden, Sr.
*Assistant Examiner*—Imad Soubra
(74) *Attorney, Agent, or Firm*—Welsh & Katz, Ltd.

(57) ABSTRACT

An apparatus for providing sterilant to a packaging machine is provided. The apparatus comprises a conduit, for a predetermined mix of atomized hydrogen peroxide and air, within a heat exchanger. The heat exchanger is a conduit for steam heat under pressure and comprises and inlet for the steam and an outlet for condensation formed by cooling steam. As the pressurized steam surrounds the conduit heat is transferred to the atomized hydrogen peroxide and air causing the mixture to vaporize. An outlet for hydrogen peroxide vapor is provided at or near a sterilization location in a packaging machine, allowing the vapor to aid in the sterilization of packaging.

10 Claims, 3 Drawing Sheets

METHOD AND APPARATUS FOR VAPORIZING STERILANT HYDROGEN PEROXIDE

FIELD OF THE INVENTION

The present invention is directed to a method and apparatus for producing vaporized hydrogen peroxide. More particularly, the invention is directed to a method and apparatus for producing sterilant grade hydrogen peroxide for use in form, fill and seal packaging machines.

BACKGROUND OF THE INVENTION

Food products are often packaged in containers that have been sterilized to prolong shelf life of the contents. Such food products can include, for example, milk, juice, dried and/or particulate foods such as soups and the like.

When these products are packaged under aseptic packaging conditions, they can be stored for a substantial period of time at room temperatures without spoilage. The packaging processes require effective sterilization of the packaging material prior to filling the container formed from the packaging material. These containers includes, for example, well-known gable-top carton, as well as other like product storing containers.

In order to achieve the desired sterilization of the container to provide maximum practicable shelf life for the product, the containers are sterilized after bottom-forming and prior to filling with the product. The entire operation including container forming, bottom sealing, sterilization, filling and top sealing can be carried out in a form, fill and seal packaging machine, such as a Tetra Rex® packaging machine available from Tetra Pak®, Inc. of Vernon Hills, Ill.

In a typical form, fill and seal packaging machine, a carton is erected from a tubular form and is placed on a mandrel. The bottom panels of the carton are folded and sealed to one another as the carton is indexed through the mandrel stations. Subsequent to bottom forming, the carton can have a fitment, such as the resealable plastic spout now available on containers, fitted and sealed thereto. Subsequent to fitment attachment, the carton is sterilized and is subsequently conveyed through the form, fill and seal packaging machine for filling and top fin sealing. The formed, filled and sealed containers are then discharged or off loaded from the machine for subsequent packaging and distribution.

Various devices and arrangements have been and are currently used to sterilize cartons on known form, fill and seal packaging machines. As disclosed in U.S. Pat. No. 6,094,887 to Swank, which patent is assigned to the Assignee of the present application and which patent is incorporated by reference herein, it is known to use ultraviolet energy, hydrogen peroxide, and a combination of UV energy and hydrogen peroxide to provide effective sterilization of containers. While various combinations of UV energy and hydrogen peroxide have been found to provide effective sterilization, the use of these two techniques adds considerably to not only the capital cost of the equipment, but the overall carton processing costs.

Known hydrogen peroxide application systems utilize electric heaters for heating and vaporizing hydrogen peroxide for subsequent application to the containers within the form, fill and seal machine. While these electric heaters work effectively, it has been found that the control systems for these heaters can be quite complex in that the temperature of the vapor-phase hydrogen peroxide must be measured so that an appropriate power can be supplied to the heaters. Such an arrangement requires temperature sensors as well as additional control equipment in order to maintain the vapor-phase hydrogen peroxide temperature within an acceptable range. It has also been found that electric heaters require a prolonged period for warming up after the equipment has been taken out of service. This can result in improper hydrogen peroxide vapor temperatures as well as the condensation of hydrogen peroxide on the electric heater elements.

It has also been found that electric heaters cannot always adequately control the output of vapor-phase temperature of the hydrogen peroxide. As such, hydrogen peroxide use may be greater than actually required thus increasing the overall process and costs.

Systems for vaporizing hydrogen peroxide are also known in which steam is intimately mixed with a liquid phase hydrogen peroxide solution which steam-hydrogen peroxide mixture is then applied to the containers. This technique has drawbacks in that it dilutes the hydrogen peroxide which can result in a less than optimal hydrogen peroxide solution concentration. In addition, such a system requires the storage of highly concentrated hydrogen peroxide which is undesirable. Accordingly, there exists a need for an apparatus and method for vaporizing hydrogen peroxide. Desirably, such an apparatus and method reduces or eliminates the possibility of diluting the vapor-phase hydrogen peroxide from a preset, desired concentration. Most desirably, such a method and apparatus permits rapid "heat up" and a controlled vapor-phase hydrogen peroxide temperature.

SUMMARY OF THE INVENTION

In accordance with the present invention, an apparatus for producing vaporized hydrogen peroxide, comprising a heat exchanger having an input for steam under pressure and an output for condensation and a conduit, extending within said heat exchanger, is provided. The conduit comprises an input for atomized hydrogen peroxide and air and a discharge end, such that when steam under pressure is added to the heat exchanger and atomized hydrogen peroxide and air traverse the conduit through the heat exchanger, the atomized hydrogen peroxide and air are heated and discharged through the conduit outlet as vapor.

In the preferred embodiment of the present invention, the conduit is a coiled tube which is placed inside a cylindrical tube. Atomized hydrogen peroxide and air flow through the coiled tube while steam under pressure is forced into the surrounding cylinder at a first end and is allowed to escape at a second end. The heat from the steam is thereby transferred from the steam to the coiled tube and the atomized hydrogen peroxide and air; vaporizing the hydrogen peroxide.

The coiled tube of the present invention is advantageously made of heat conductible metal which does not react to hydrogen peroxide, such as stainless steel or a composite metal having such properties as excellent heat conductability, malleability for easy shaping, inertness in the presence of hydrogen peroxide, and strength and durability. The device, of the preferred embodiment of the present invention, comprises a cylinder, having an input for steam and an outlet for condensation, with the conduit contained therein, the heat from stream being transferred to the conduit, to heat its contents, as the steam passes about the conduit.

The apparatus of the preferred embodiment of the present invention is advantageously connected to a packaging machine and the vapor is used to help sterilize packaging. The packaging is used for such products as milk and juice.

A more detailed explanation of the invention is provided in the following description and claims and is illustrated in the accompanying drawings.

DETAILED DESCRIPTION OF THE PREFERRED EMBODIMENTS

Figure 1:
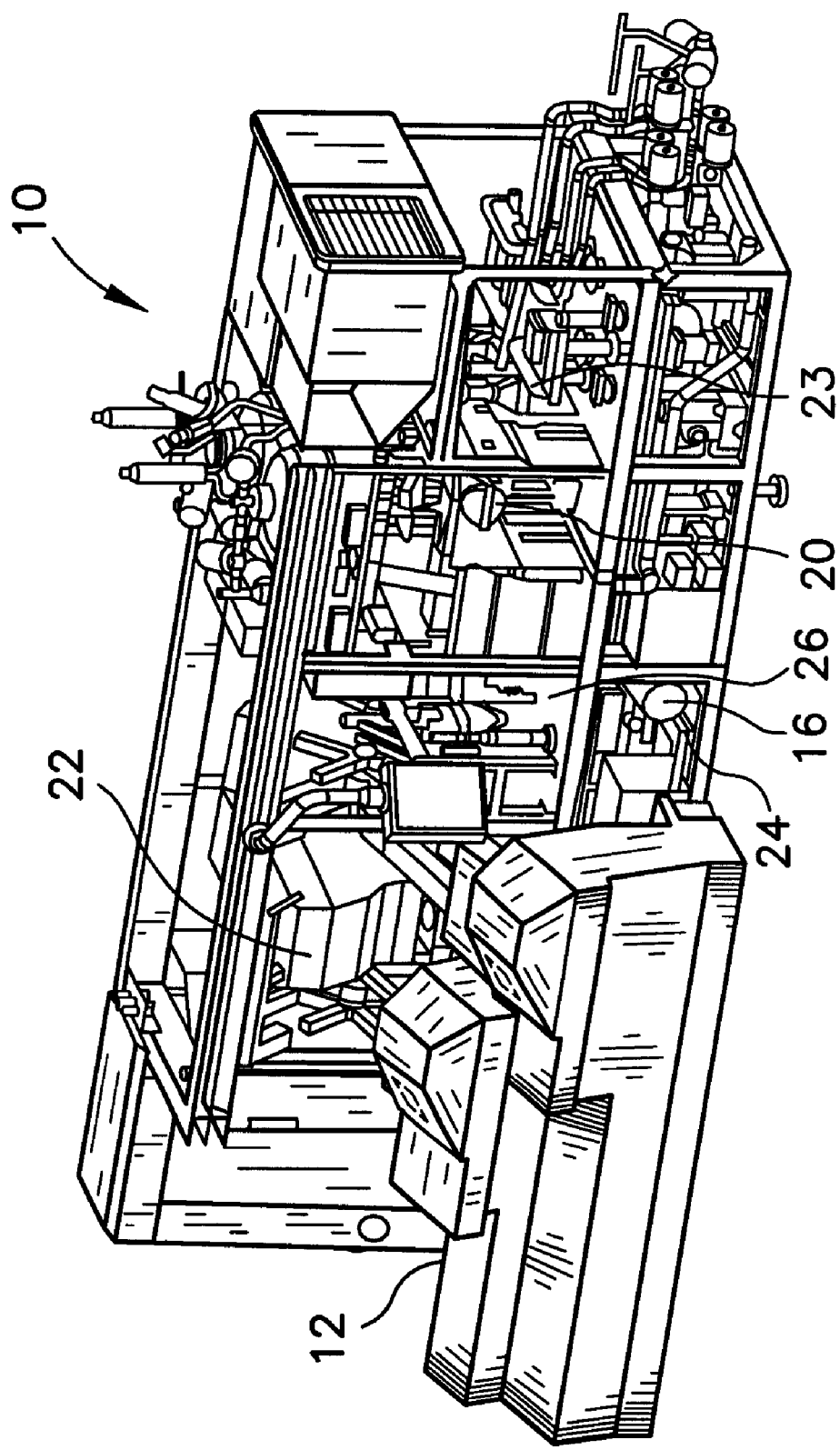
FIG. 1 illustrates an exemplary form, fill and seal packaging machine that includes a steam heated hydrogen peroxide vapor generator embodying the principles of the present invention

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

Referring now to the figures and in particular FIG. 1 there is shown an exemplary form, fill and seal packaging machine 10 embodying the principles of the present invention. Such a machine 10 is commercially available from Tetra Pak®, Inc., Vernon Hills, Ill. and is manufactured under the trademark TETRA REX® packaging machine 10. A conventional form, fill and seal packaging machine 10 includes a carton magazine 12 for storing flat, folded, carton blanks 13, a carton erection station 14 and a bottom forming and sealing station 22. The machine 10 further includes a sterilization station 16 for sterilizing the cartons and further includes a filling station 20 at which the cartons are filled with product and a top sealing station 22 at which the top panels of the cartons are pre-folded and subsequently sealed to one another. The cartons are then off loaded from the form, fill and seal packaging machine 10. An exemplary form, fill and seal packaging machine 10 is disclosed in U.S. Pat. No. 6,012,267 to Katsumata which patent is owned by the Assignee of the present application and which patent is incorporated herein by reference.

Figure 2:
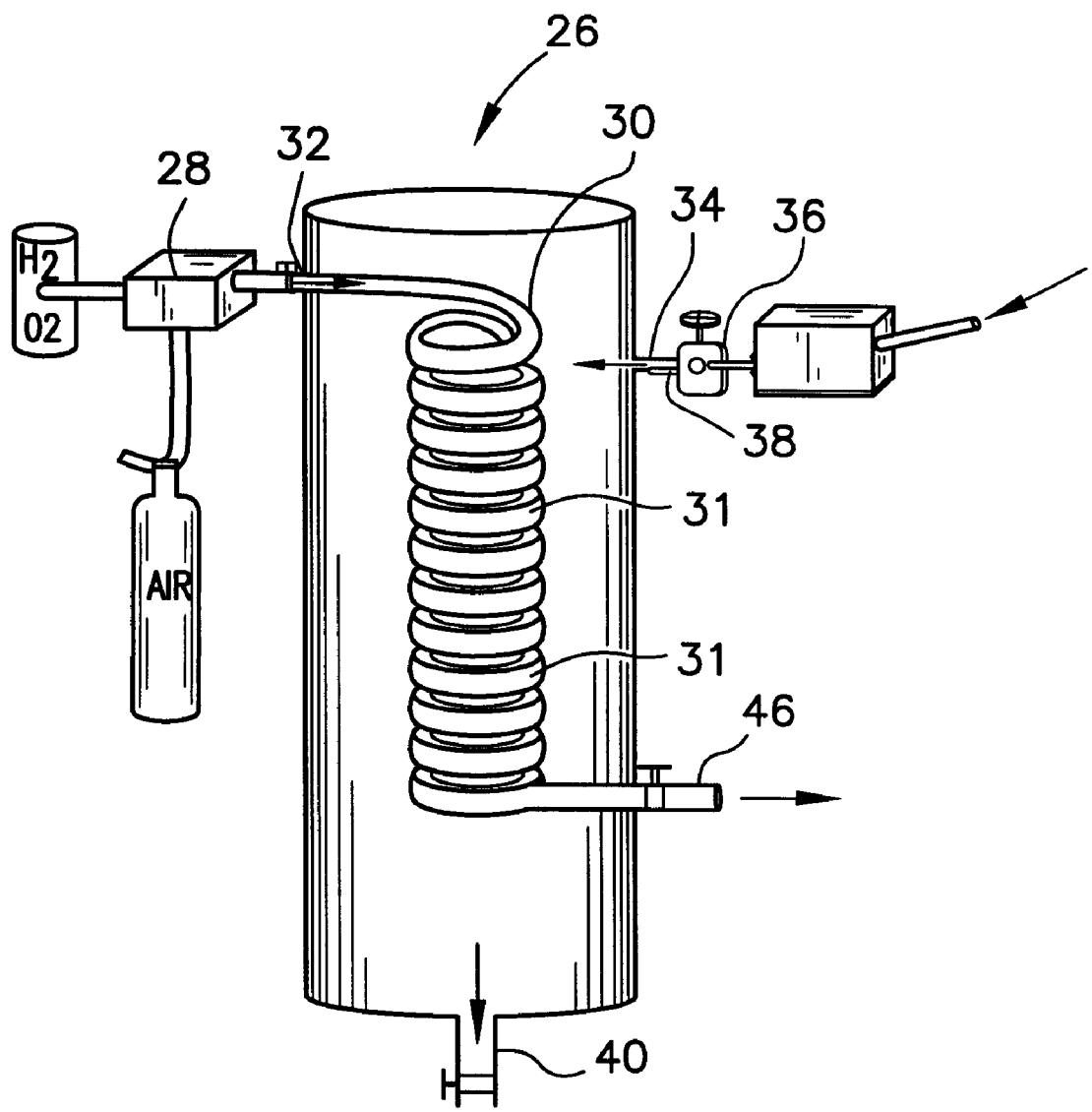
FIG. 2 is a schematic illustration of one embodiment of a system for providing vapor-phase hydrogen peroxide embodying the principles of the present invention; and, FIG. 3 illustrates a steam heater embodying the principles of the present invention.
Figure 3:
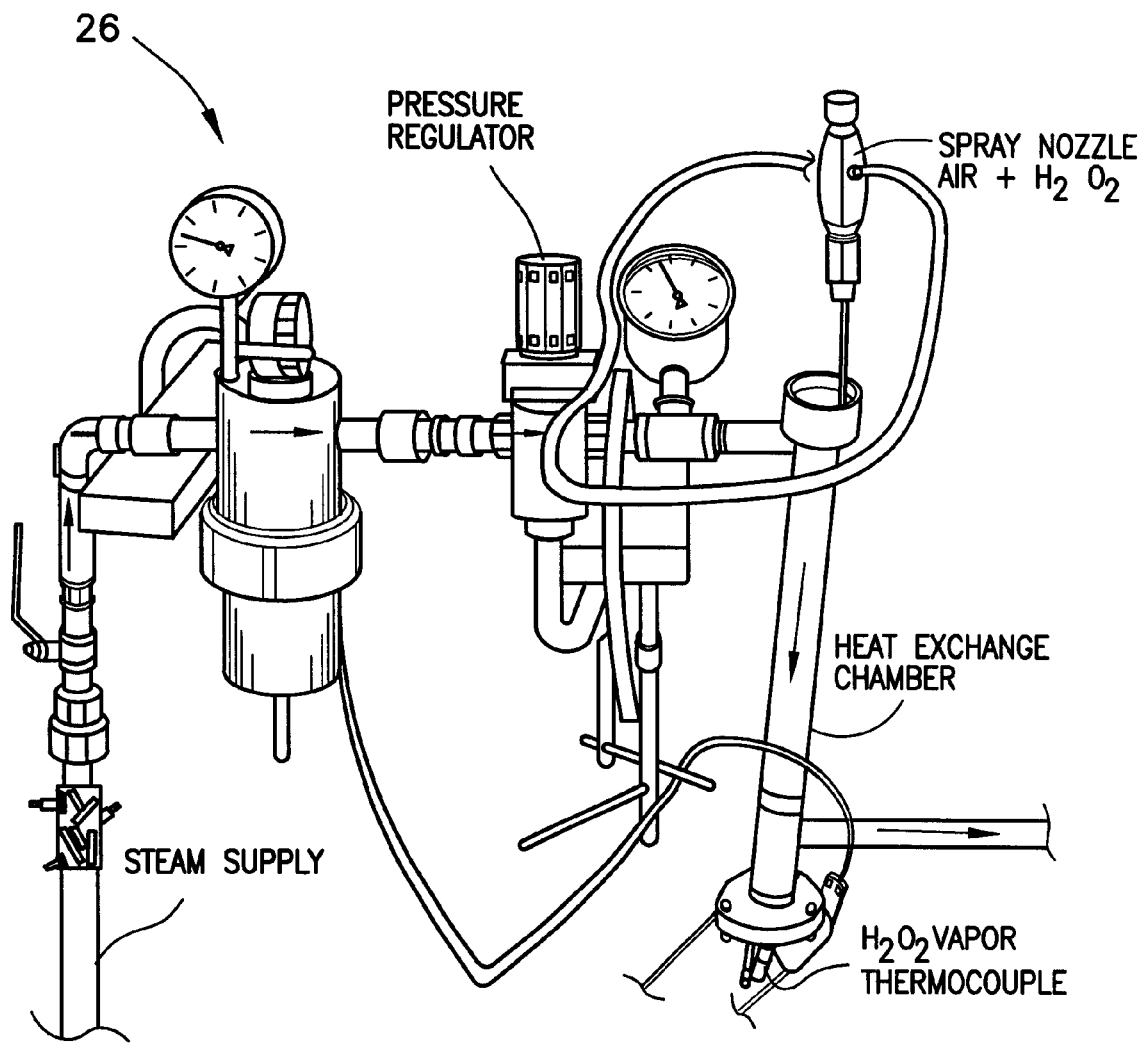

The sterilization station 16 is positioned between the bottom forming and sealing station 22 and the filling station 20. The sterilization station 16 can include one or more ultraviolet energy generating devices 24, such as that disclosed in U.S. Pat. No. 6,094,887 to Swank. The sterilization station 16 further includes a hydrogen peroxide vapor generating system 26, as shown in FIGS. 2 and 3. The hydrogen peroxide vapor generating system 26 includes generally, an atomizer 28 and a heat exchanger 30. The heat exchanger 30 can be of the coiled tubing type in which the atomized hydrogen peroxide flows through the coils 31 in a primary side 32 of the heat exchanger 30. In a secondary side 34 of the heat exchanger 30, isolated from the hydrogen peroxide relative to fluid contact, steam is provided to the heat exchanger 30.

The steam is supplied from a steam supply through a pressure regulator 36. Steam from the pressure regulator 36 is directed into the inlet 38 of the secondary side 34 of the heat exchanger 30 at saturated conditions. Condensate is discharged from the heat exchanger 30 through a condensate outlet 40.

Hydrogen peroxide is provided through an atomizer 28 at which the hydrogen peroxide is mixed with air. As the hydrogen peroxide flows through the coils 31 in the heat exchanger 30, it is heated to essentially the same temperature as the inlet 38 steam. The hydrogen peroxide exists the heat exchanger 30 at a discharge end 46 thereof and passes over a hydrogen peroxide vapor thermocouple 48. The hydrogen peroxide then is placed into packaging machine to assist in the sterilization of product packaging.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A method for producing vaporized hydrogen peroxide, comprising:

a heat exchanger having an input for steam under pressure and an output for condensation;

a conduit, extending within said heat exchanger, having an input for atomized hydrogen peroxide and air and a discharge end, such that when steam under pressure is added to the heat exchanger and atomized hydrogen peroxide and air traverse the conduit through the heat exchanger, the atomized hydrogen peroxide and air are heated and discharged through the conduit outlet as vapor.

2. The method of claim 1, wherein the conduit is a coiled tube.

3. The method of claim 2, wherein the coiled tube conduit is comprised of stainless steel.

4. The method of claim 2, wherein the coiled tube conduit is comprised of a metal having the properties of heat conduction, strength, durability and malleability.

5. The method of claim 1 wherein the heat exchanger comprises a cylinder having an input for steam and an outlet for condensation, the heat from stream being transferred to the conduit, to heat its contents, as the steam passes about the conduit.

6. The method of claim 1, wherein the apparatus is connected to a packaging machine and the vapor is used to sterilize packaging.

7. An apparatus for producing vaporized hydrogen peroxide, comprising:

a conduit;

a heat exchanger, comprising a cylinder having an input for steam and an outlet for condensation, the heat from stream being transferred to the conduit, to heat its contents, as the steam passes about the conduit;

the conduit comprising a coiled tube, extending within said heat exchanger, having an input for atomized hydrogen peroxide and air and a discharge end, such that when steam under pressure is added to the heat exchanger and atomized hydrogen peroxide and air traverse the conduit through the heat exchanger, the atomized hydrogen peroxide and air are heated and discharged through the conduit outlet as vapor.

8. The method of claim 7, wherein the coiled tube conduit is comprised of stainless steel.

9. The method of claim 7, wherein the coiled tube conduit is comprised of a metal having the properties of heat conduction, strength, durability and malleability.

10. The method of claim 7, wherein the apparatus is connected to a packaging machine and the vapor is used to sterilize packaging.

* * * * *